(12) United States Patent
Tennant (10) Patent No.: US 10,335,713 B2
(45) Date of Patent: Jul. 2, 2019

(54) EXTRACTION APPARATUS AND METHOD (71) Applicant: Nicholas Tennant, Royal Oak, MI (US)

(72) Inventor: Nicholas Tennant, Royal Oak, MI (US)

(73) Assignee: Precision Extraction Corporation, Troy, MI (US)

( * ) Notice: Subject to any disclaimer, the term of this patent is extended or adjusted under 35 U.S.C. 154(b) by 0 days.

(21) Appl. No.: 15/075,017

(22) Filed: Mar. 18, 2016

(65) Prior Publication Data

US 2017/0043276 A1    Feb. 16, 2017

Related U.S. Application Data

(60) Provisional application No. 62/134,621, filed on Mar. 18, 2015.

(51) Int. Cl.
*B01D 11/02* (2006.01)
*C07D 311/80* (2006.01)

(52) U.S. Cl.
CPC ...... *B01D 11/0296* (2013.01); *B01D 11/0288* (2013.01); *C07D 311/80* (2013.01)

(58) Field of Classification Search
CPC ............ B01D 11/0296; B01D 11/0288; C07D 311/80
See application file for complete search history.

(56) References Cited

U.S. PATENT DOCUMENTS

| 7,640,756 B2* | 1/2010 | Brahmbhatt | F26B 5/06 34/287 |
| 9,289,697 B2* | 3/2016 | Masetto | C02F 1/20 |
| 9,669,328 B2* | 6/2017 | Jones | C11B 1/10 |

* cited by examiner

*Primary Examiner* — Randy Boyer
*Assistant Examiner* — Juan C Valencia (57) ABSTRACT

An extraction apparatus and a processes for preparing extracts of natural products, such as plant material, and for preparing purified extracts from crude extracts of natural products by extraction with a non-polar solvent hot gas.

15 Claims, 7 Drawing Sheets

EXTRACTION APPARATUS AND METHOD

CROSS-REFERENCE TO RELATED APPLICATION

The present disclosure claims priority to U.S. Provisional Patent Application Ser. No. 62/134,621, filed Mar. 18, 2015, to TENNANT et al and titled: EXTRACTION APPARATUS AND METHOD, the contents of which are incorporated herein for all purposes.

FIELD

The present disclosure relates to an extractor apparatus and a processes for preparing extracts of natural products, such as plant material, and for preparing purified extracts from crude extracts of natural products by extraction with a non-polar solvent hot gas.

BACKGROUND

It has been known for some time to use an extraction apparatus to expose a plant and/or flower to a solvent for the purpose of extracting various constituent components from the plant or flower and to then remove the solvent from the extracted components. The extracted components may be used in any variety of foods, goods and compositions. While extraction apparatuses are generally known for use in extracting various constituent components of plant material, the disclosure of U.S. Pat. No. 7,622,140 published Nov. 24, 2009, to Whittle et al, and entitled Processes For Preparing A Cannabinoid-Rich Extract From *Cannabis* Plant Material, the entire contents of which are incorporated herein by reference for all purposes, discloses a particular process and an apparatus for the useful separation of certain plant constituents. Despite the many known types of extraction devices and apparatuses, there remains no device which is highly capable of a controlled, efficient and effective extraction in a thoroughly portable device.

While there have been many attempts by others to address this long known need, including the known apparatuses and processes, there remains an unmet need for an extraction apparatus and process for more efficiently, effectively and safely separating plant constituent components.

DETAILED DESCRIPTION

Figure 1:
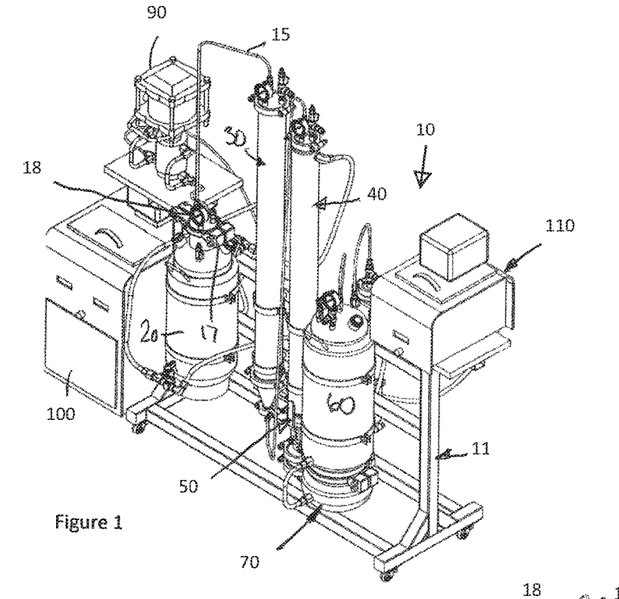
FIG. 1 is a front perspective view of an extraction apparatus according to the present disclosure.
Figure 2:
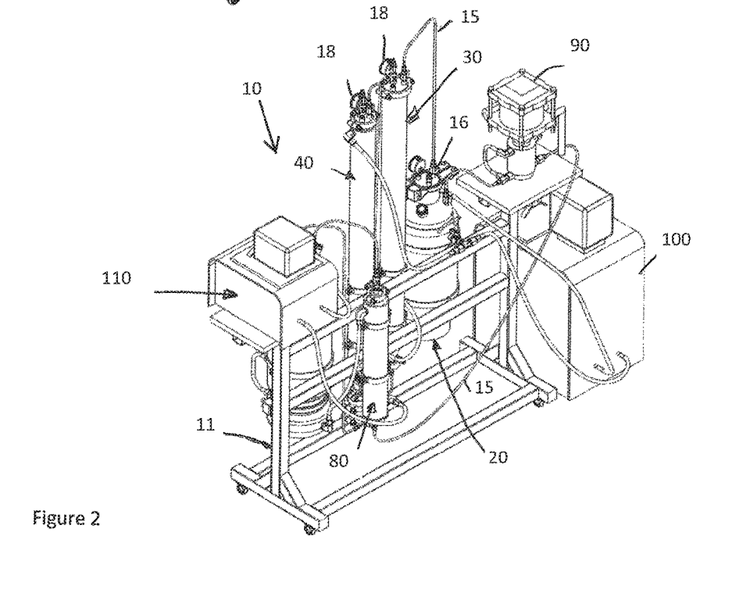
FIG. 2 is an alternate back perspective view of the extraction apparatus of FIG. 1.
Figure 3:
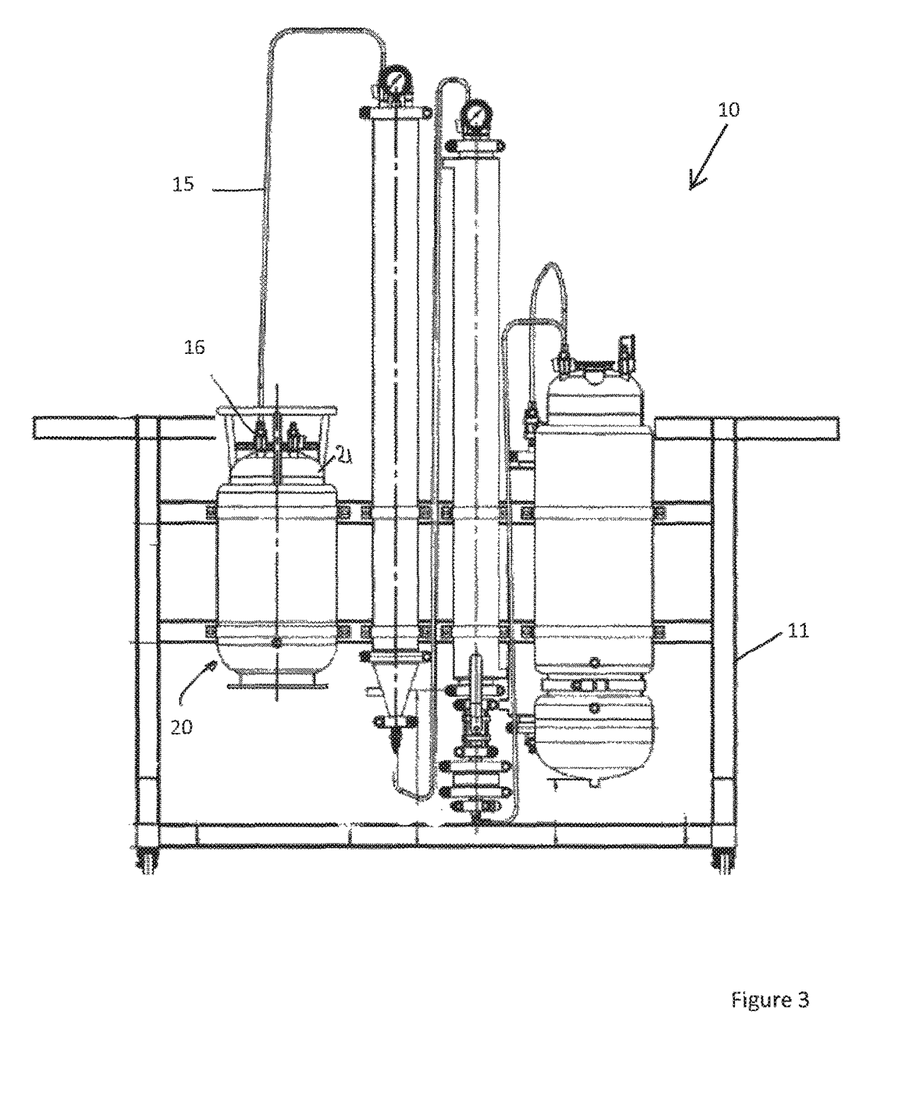
FIG. 3 is a plan front view of the extraction apparatus of FIG. 1.

Referring in general to all of the figures, and initially in particular to FIGS. 1 through 3, there is illustrated an extraction apparatus 10 according to the present disclosure and capable of operating according to a method for more efficiently, effectively and safely extracting constituent materials and components from an amount of raw, plant or flower material. The extraction apparatus 10 may have particular use in isolating, via short path distillation or extraction, specific components and combinations of components of the plant or flower material.

The extraction apparatus 10 of the present disclosure may be capable of providing sufficient control of the extraction process to more specifically isolate particularly components and combinations of components of the plant or flower material being extracted, and may provide improved control and process for obtaining the components to a molecular level. In one specific application, the extraction apparatus 10 may be used to isolate specific cannabinoids or groups of cannabinoids, as well as isolating THC and other specific constituent components and combinations to obtain an extraction product. More particularly, the present disclosure provides an extraction apparatus 10 including various components making it specifically possible to extract a particular terpene profile from a plant or flower material in a portable extraction apparatus 10. The portable extraction apparatus 10 may accomplish the above while using a far more efficient and effective process. The extraction apparatus 10 may be operated to perform an extraction process preferably using a non-polar solvent. The extraction apparatus 10 may use a light hydrocarbon solvent. The extraction apparatus 10 may provide for greater control and efficiency of the extraction process such that a user may have greater control to obtain particular flavor profiles as well as desired quality, flavors and combinations of cannabinoids.

The extraction apparatus 10 may preferably include a plurality of sub-components mounted to a wheeled, mounting rack 11. The mounting rack 11 may preferably include a lower base portion, a plurality of uprights coupled to and extending from the lower base portion and a plurality of cross members extending between and coupled with the uprights. A first upright may include an upper surface and a second upright may include a second upper surface, as best shown in FIGS. 1 through 3. The mounting rack 11 may preferably be comprised of any material, including, in one particular embodiment, a metal such as stainless steel. The mounting rack 11 may be comprised of any known or appropriate material for use with the extraction apparatus 10 and for carrying out the extraction methods.

The extraction apparatus 10 may include the solvent tank 20, the material column 30, the cryogenic column 40, the lipid filtering column 50, the collection chamber column 60, the expansion filter column 80, the recovery pump 90, the cryogenic chiller 100, and the recirculating heat 110, all of which are coupled using a plurality of hoses 15 and having a plurality of ¼" shut off valves 16 and gauges 18. The components of the extraction apparatus 10 may be set up to create an extraction process flow as best shown by the FIG. 10 which is continually referenced during the present disclosure.

The solvent tank 20 may be coupled to the material tank or column 30 by a hose 15 coupling the outlet of the solvent tank 20 to an inlet on the lid of the material column tank 30, the bottom of the material column 30 may be coupled to the inlet in the top of the top of the cryogenic column 40. The cryogenic column 40 and the lipid filtering column 50 are integrated such that material (i.e., solvent and dissolved plant constituent components) leaving the cryogenic column 40 passes to the lipid filtering column 50 for removing the coagulated material constituent components and to separate them from the solvent and the dissolved constituent components from the plant material. The bottom of the lipid filtering column 50 is coupled (by a hose 15) to the inlet of the collection chamber column 60 which is integrated with the collection bowl 70 so that the solvent and the dissolved extracted constituent components from the material flowing there through may be collected in the collection bowl 70. The dissolved extracted constituent components and the hydrocarbon solvent may then move to one of the expansion filter column 80 and the hydrocarbon recovery pump 90. The hydrocarbon solvent removed by the hydrocarbon recovery pump 90 is then conveyed back to the solvent tank 20 as explained in greater detail herein.

Figure 4:
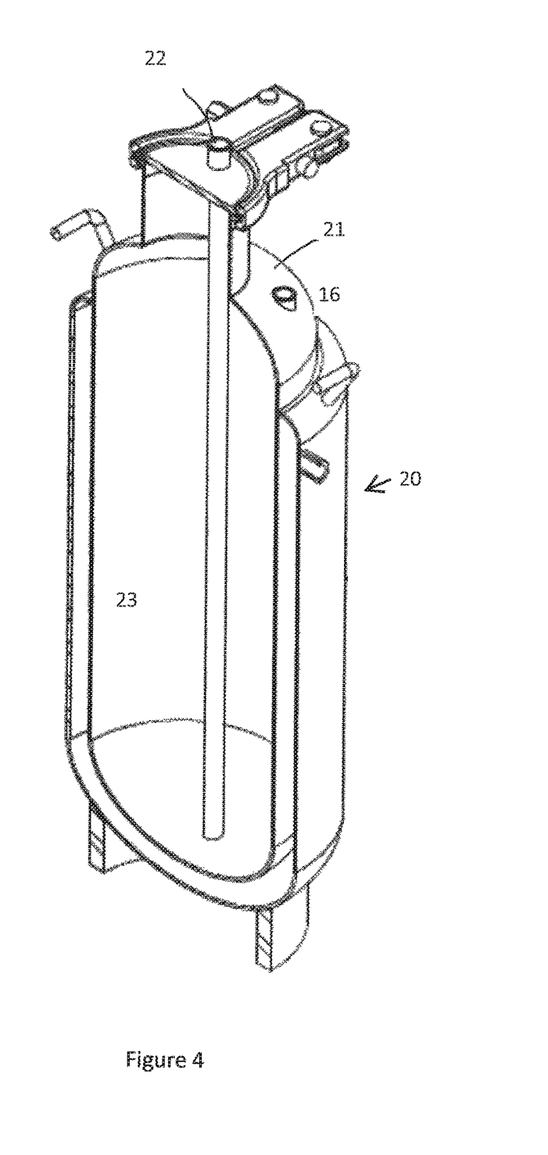
FIG. 4 is a partial perspective view of a solvent tank of the extraction apparatus of FIG. 1.

Referring generally to FIGS. 1 through 3, and in particular to FIG. 4, the extraction apparatus 10 may include the solvent tank 20 generally having the construction and proportions as shown in the figures. The solvent tank 20 may include a lid or cover 21. The solvent tank cover 21 may include a plurality of passages for coupling the solvent tank 20 to the other components of the extraction apparatus 10. The solvent tank 20 may preferably have a generally cylindrical shape and be made from any known or appropriate material for use in producing an (human) edible product, including, in particular, a stainless steel such as 304SS. The solvent tank 20 may be coupled to the other components using a hose 15 including a shutoff valve 16 for isolating the solvent tank 20 from all other components of the extraction apparatus 10.

Figure 10:
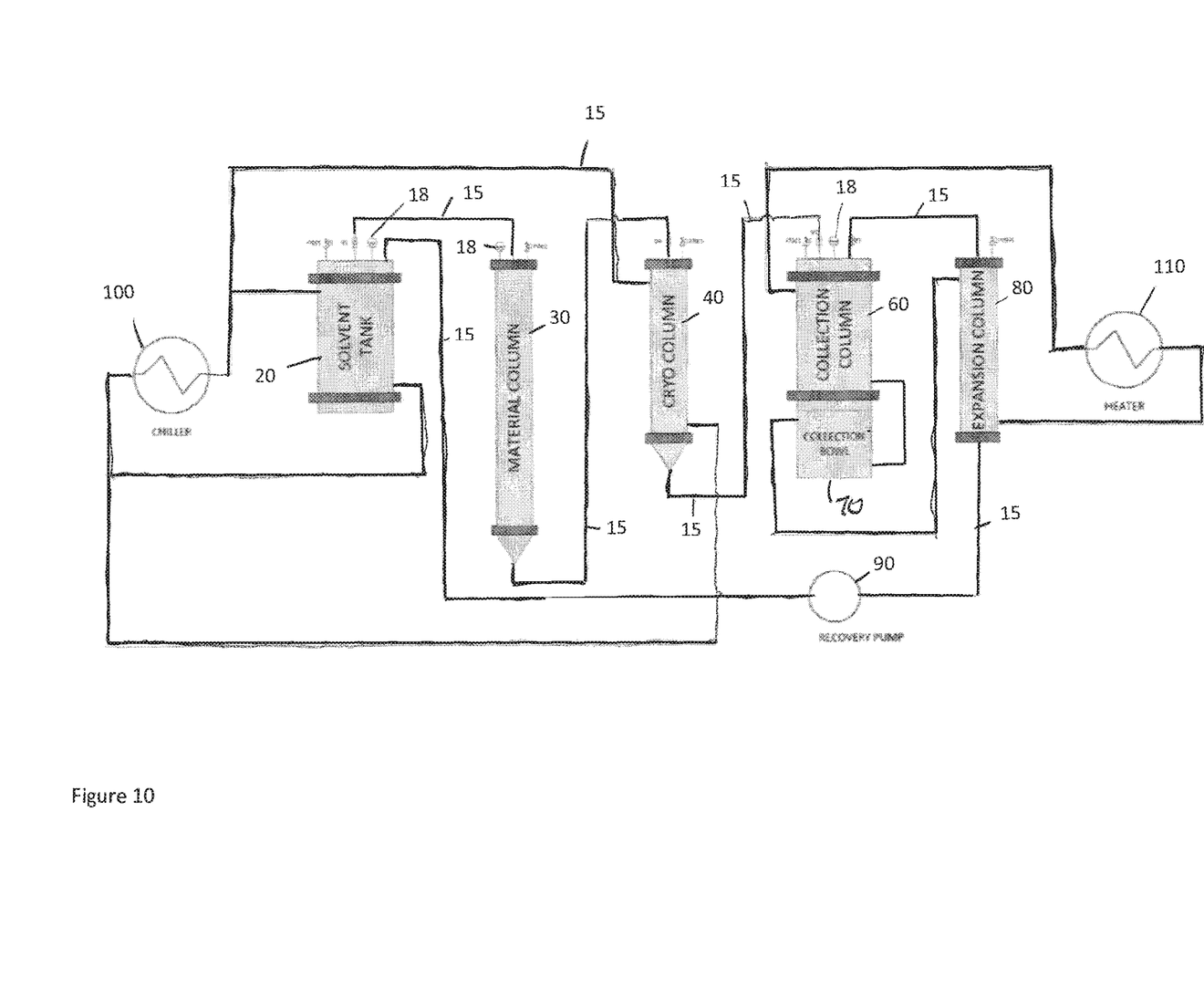
FIG. 10 is a schematic flow diagram of the extraction apparatus of FIG. 1.

The solvent tank 20 cover may also include a passage for receiving a high pressure vent down 17 as best shown in FIG. 10. The high pressure vent down 17 may be adjusted to have a relief, pressure setting of approximately 150 psi such that if the pressure in the solvent tank 20 is above the relief pressure setting (i.e., 150 psi), then the high-pressure vent down 17 will open and reduce the pressure in the solvent tank 20 below the relief pressure setting. The cover of the solvent tank 20 may also include a passage for receiving a compound pressure gauge 18 as best shown in FIG. 11. The high-pressure vent down 17 and the pressure gauge 18 may be coupled to the cover 21 of the solvent tank 20 using an end cap as is generally understood. The end cap may be coupled to the opening in the cover 21 of the tank 20 and sealed using a 1 inch Viton gasket (not shown). The end cap includes a passage for coupling the high-pressure vent down 17 and the pressure gauge 18. The cover of the solvent tank 20 may further include a male JIC to male NPT union i straight hydraulic hose adapter as best shown in FIG. 14.

Once the solvent tank 20 is completely assembled and isolated from the rest of the extraction apparatus 10 by closing the shutoff valves 16, a vacuum pump (not shown) may be coupled to the tank 20 and a negative pressure (or vacuum) of approximately −30 inches of Mercury (in-Hg) may be established in the solvent tank 20 to remove as much oxygen ($O_2$). The vacuum pump may then be removed and a hydrocarbon solvent fill tank (not shown) may then be coupled to the solvent tank 20.

Once the solvent fill tank is coupled to the solvent tank 20, the valve 16 may be opened and liquid solvent filled in an internal chamber 23 of solvent tank 20 to approximately 80% of the volume of the internal chamber 23. It should be understood that other percentages may be used as may be desirable for achieving a particular outcome of the extraction process. The solid tank 20 may include sight glasses for viewing the level of the liquid hydrocarbon solvent therein. While it is possible to fill the solvent tank 20 at any time after the vacuum is established and an appropriate temperature is achieved (as described below), it is commonly not done until the entire system is prepared.

Figure 5:
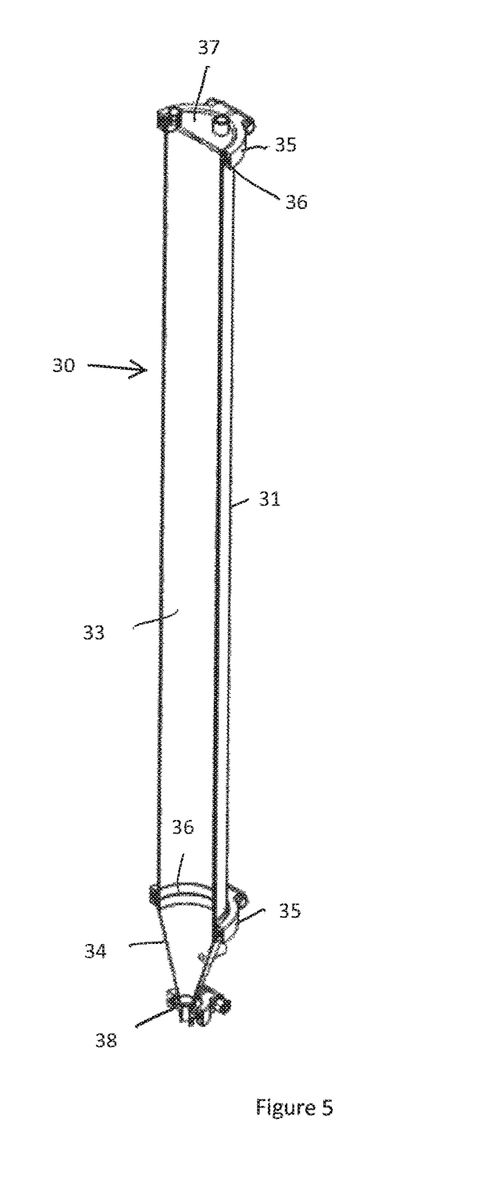
FIG. 5 is a partial perspective view of a material column of the extraction apparatus of FIG. 1.

Referring generally FIGS. 1 through 3, and in particular to FIG. 5, the components and details of the material column 30 are shown in partial perspective view in greater detail. The material column 30 may be a generally elongate cylindrical shaped body 31 including an inner chamber 33 extending between a first or upper end and a second or lower end. The material column 30 may further include a material column reducer 34 coupled to the lower end of the material column body using a 4 inch high-pressure tri-clamp 35 as shown in FIG. 5 and which may be sealed using a 4 inch Viton gasket 36. The first or upper end of the material column 30 may include a material column end cap 37 coupled to the upper end of the material column body using a 4 inch high-pressure tri-clamp 35 and may be sealed using a 4 inch Viton gasket 36. The upper material column end cap 37 may further include a pressure gauge 18 (FIG. 2) and a coupling for coupling the other end of the hose 15 from the solvent tank 20.

Figure 6:
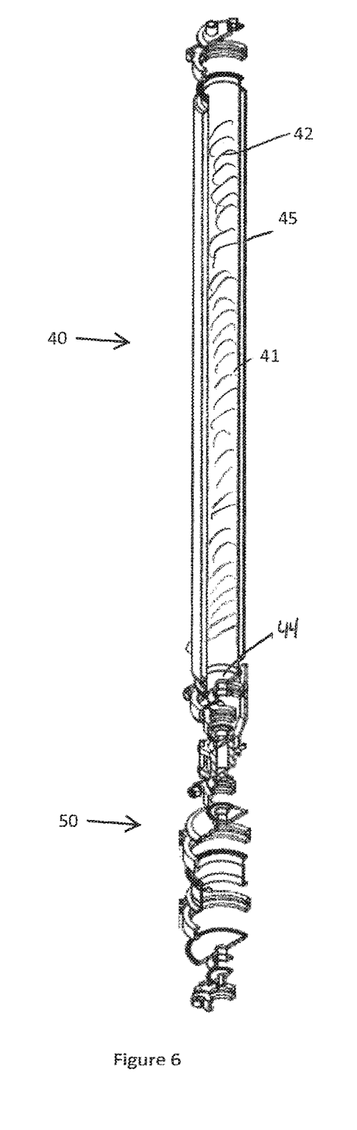
FIG. 6 is a partial perspective view of a cryogenic column and a lipid filtering column of the extraction apparatus of FIG. 1.

The second or lower end of the material column 30 may include a material column end cap 38 coupled to the lower end of the material column reducer 34. The extractor apparatus 10 may further include a hose 15 extending from a coupling on the lower end cap of the material column reducer 34 and having a second end connected to a coupling of the inlet of the cryogenic column 40 as shown in FIG. 6.

The cryogenic column or tank 40 is a generally cylindrically shaped member also made from a metal material such as 304 stainless steel. The inlet to the cryogenic column 40 may be located on one side (although it may be located in other positions) and may include a ¼" NPT coupling which may be coupled to a coiled ¼ inch tubing 42 located within a chamber or passage 41 in the cryogenic column 40, as best shown in FIG. 6. The coiled tubing 42 generally extends the length of the cryogenic column 40 to the generally opposite end of the chamber 41 within the cryogenic column 40 including an endplate 44 closing one end of the chamber or passage 41 within the cryogenic column 40 and having the end of the tube 42 exiting and passing through the endplate in one alternate embodiment. In the present embodiment, the column 40 may include a jacket 45 including an inlet and an outlet 46 for passing cryogenically cooled material for reducing the temperature within the passage 41. The cryogenic column 40 may further include a chiller inlet located on the wall of the cryogenic column 40 and including a coupling for connection to a cryogenic chiller hose coupled to the outlet of the cryogenic chiller 100. The chiller inlet may be located near the top of the cryogenic column 40. The cryogenic column 40 may further include a chiller outlet located on the wall of the cryogenic column 40 (which may be located near the bottom of the chamber) and including a coupling for connection to a cryogenic chiller hose coupled to the inlet of the cryogenic chiller 100. Accordingly, the coiled tubing 42 within the chamber 41 may be contacted and cooled by the cryogenic cooler 100 material circulated through the chamber 41 of the cryogenic column 40. The cryogenic cooler 100 circulating the material in the cryogenic dewaxing column 40 may preferably keep the temperature at approximately −40° F. and may preferably operate as low as −120° F. depending upon the performance criteria of the cryogenic cooler 100 and the required performance specifications of the particular extraction process.

Figure 7:
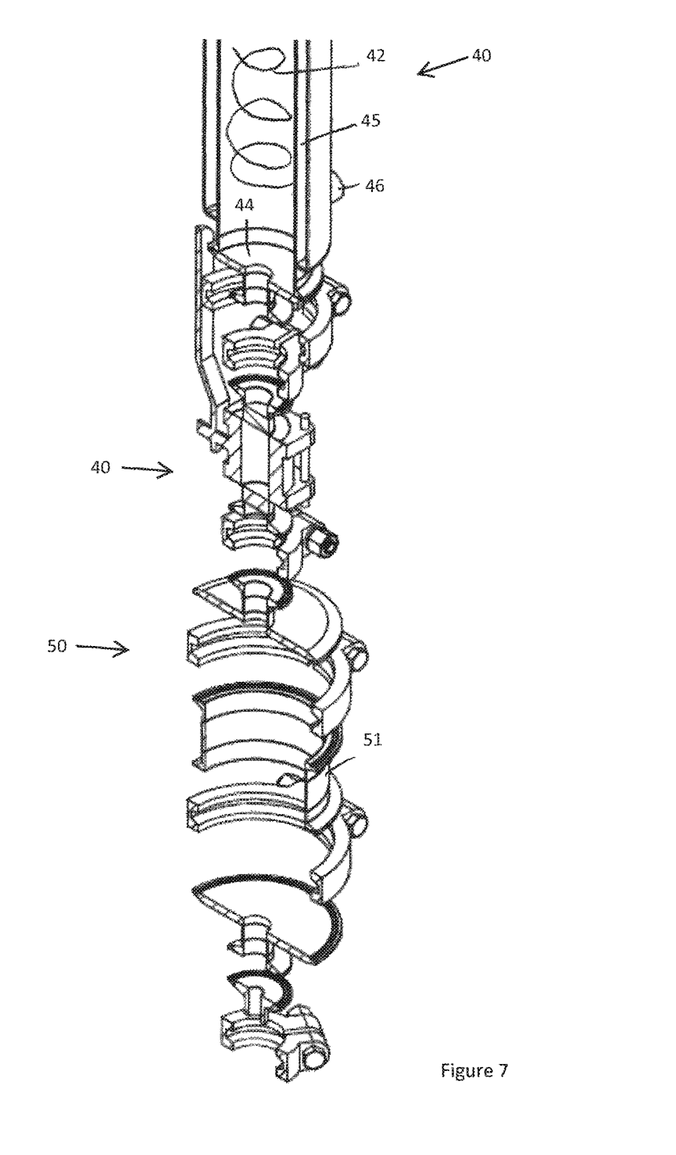
FIG. 7 is a partial, expanded, perspective view of the bottom end of the cryogenic column and lipid filtering column of FIG. 6.

The bottom of the cryogenic column 40 may be coupled to one end of a lipid filtering column 50 using the appropriate clamp and gasket and the solvent and extracted material exiting the end of the tube at the bottom of the cryogenic column 40 may be transferred to the lipid filtering column 50. The other end of the lipid filtering column 50 may be coupled to a filter stack spacer 51 having an under bore to fit inside the lipid filtering column and designed to hold a filter mesh as well as a paper lipid filter. In one particular embodiment, the paper lipid filter may be a Grade 41 quantitative, circle filter paper ashless, having a typical thickness of 220 µm, a basis weight of generally 85 g/m$^2$, and airflow rate of generally 3.4 seconds/100 mL per square inch, and other related performance specifications and made from a high-quality cotton linters material. In one embodiment, the filter stack 51 of the lipid filtering column tank 50 may include a plurality of filter spacers and a plurality of filter mesh and/or a plurality of paper lipid filters as may be desirable for achieving a particular extracted material while using the extraction apparatus 10 to perform the extraction process.

The filter stack 51 functions to trap the coagulated lipids (from the heat transfer of the cooling of the lipid filtering tank column 40) and to separate the coagulated lipids and other coagulated components of the constituent materials that are coagulated via cooling within the chamber 41 within the cooling jacket or chamber 45 of the lipid filtering column 50 and the solvent and the remaining dissolved plant material constituents and solvent (e.g., cannabinoids) may pass through the lipid column tank filter stack 51 and may be transferred from the lipid filtering column 50. As noted, in one design, the lipid filtering column tank or column 50 may preferably include the cooling chamber 45 surrounding the solvent and dissolved constituent material passage 41 for providing a cooling effect thereto.

In one alternate version of the extraction apparatus 10, a lipid column reducer may be included. The lipid column reducer may be coupled to the bottom of the lipid filtering column 50 in a manner similar to the material column reducer 34, and may further include an end cap including a coupling for coupling a hose 15 which conveys the dissolved cannabinoids and solvent to an inlet in the collection chamber lid 61 of the collection chamber column 60 as best shown in FIG. 8.

As a point of reference, the extraction apparatus 10 of the present disclosure may include a plurality of valves 16 coupled to the hoses 15 and the respective components of the extraction apparatus 10 for isolating each component of the extraction apparatus 10 for operating the method of extraction according to the present disclosure including the use of the hydrocarbon solvent for extracting the constituent materials from the plant material and for operating the closed-loop method of extraction.

Figure 8:
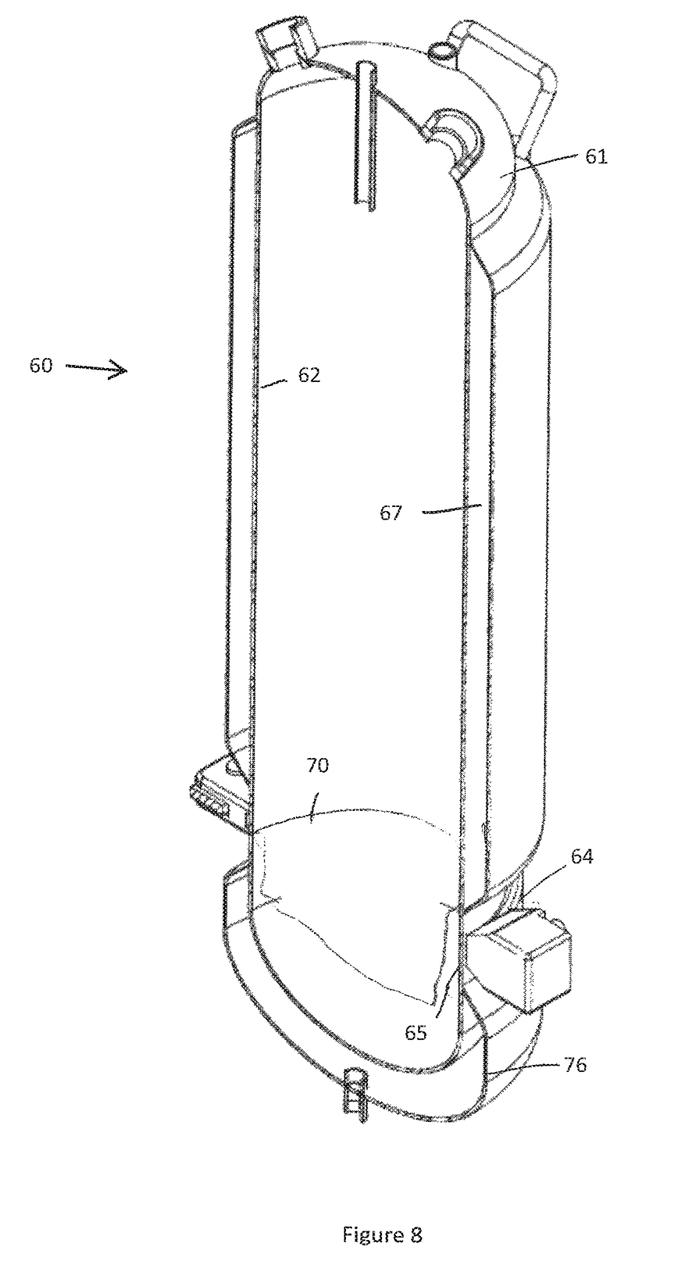
FIG. 8 is a partial, perspective view of a collection chamber column of the extraction apparatus of FIG. 1.

Referring in particular now to FIG. 8, the collection chamber column 60 may include an inner chamber 62 for receiving the material from the lipid column 50. The collection chamber lid 61 may preferably be located at, and coupled to, the top end of the chamber 62 of the column 60. The extraction apparatus 10 may further include a collection chamber bowl 70 coupled to the bottom end of the chamber column 60. The collection chamber lid 61 and the collection chamber bowl 70 may each preferably be coupled to the collection chamber column 60 using a clamp 64 including a seal 65. The collection chamber lid 61 of the collection chamber column 60 may include an outlet coupled to a hose 15 and the other end of the hose 15 may be coupled to the inlet of the expansion filter column 80 (FIG. 2). Notably, the extracted material components from the plant material from column 30 is in a generally liquid form and may be deposited in the collection chamber bowl 70 along with the liquid hydrocarbon solvent.

The collection chamber bowl 70 may include a heater jacket 76 separate from a heater jacket 67 of the collection chamber 60 for heating the extracted material and the solvent (e.g., liquid hydrocarbon) and causing the solvent to transition from a liquid to a gas while the material collects in the bowl 70. The heater jackets 67 and 76 may be heated using any known or appropriate heater and may include a recirculating heater 110 coupled to the heater jackets of the collection chamber y and the collection chamber bowl 70 (as well as the expansion/filter column 80 (FIG. 2) as described herein) and may have an operating range of between approximately 30° F. and 400° F. Once all of the hydrocarbon solvent is in the collection chamber bowl 70, the connection between the collection chamber column 60 and the material column 30 may be closed and the connection between the collection chamber y and the expansion/filter column 80 may be opened.

The recirculating heater 110 may be initiated (before during or after) to warm the contents of the collection bowl 70 which will cause the hydrocarbon solvent to boil or re-distill and transition into a hydrocarbon gas and/or vapor while the extraction material and components will remain in a liquid state in the collection chamber bowl 70. In one particular embodiment, the recirculating heater 110 may be a GSC high temperature thermostatic circulating oil bath device 110 available from Shanghai, Kankun Instrument Equipment Company, Limited.

The expansion/filter column 80 (FIG. 9 in particular) may include end caps 81 including an appropriate coupling for coupling the hoses 15 to the expansion/filter column 80. The expansion/filter column 80 may include a jacketed chamber 82 including an inner chamber 82 for receiving the gaseous/vaporous hydrocarbon solvent from the collection chamber 60 as it is boiled off from the collection chamber bowl 70 and a jacket chamber 83 including an inlet and an outlet 84 for circulating the heated fluid there through and further insuring the solvent is sufficiently heated to be completely in a gaseous form prior to being conveyed from the outlet 85 of the expansion/filter column 80 and to the inlet of a hydrocarbon recovery pump 90.

Figure 9:
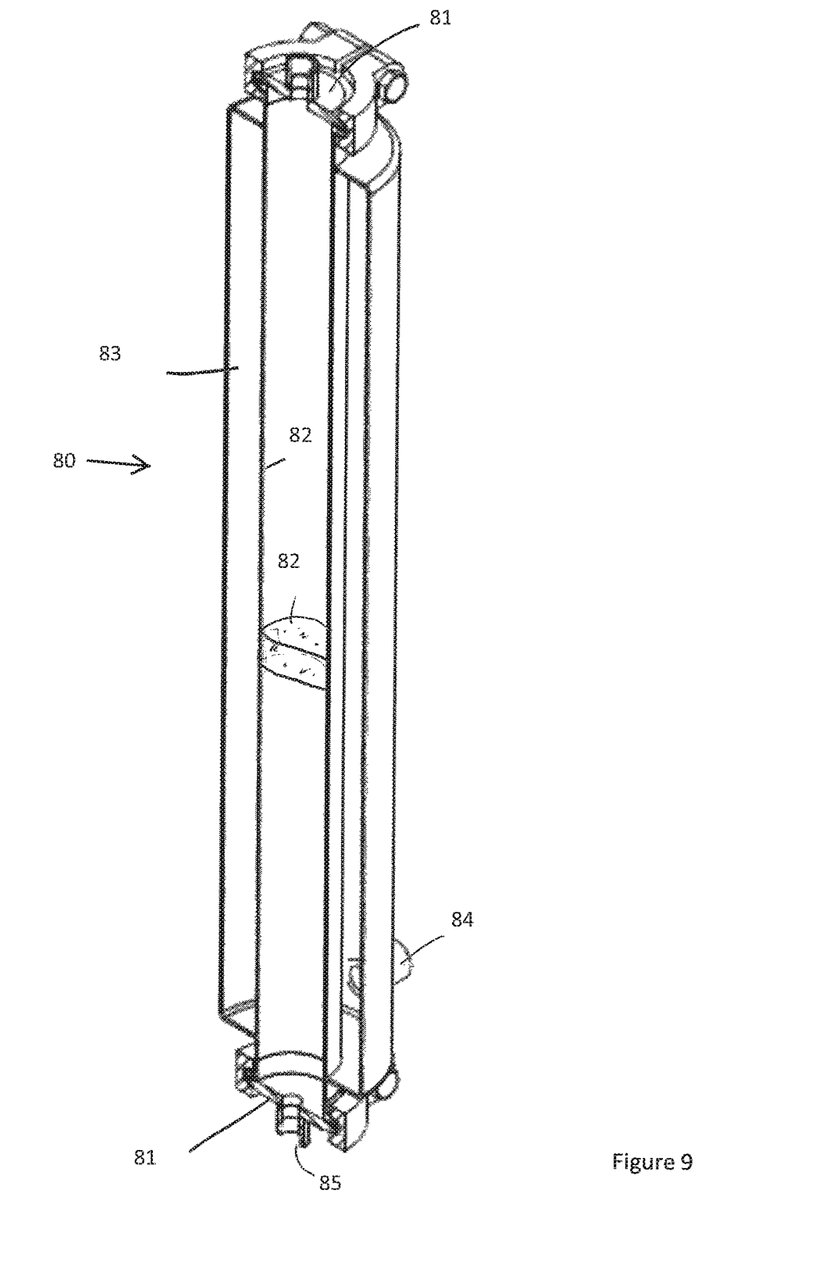
FIG. 9 is a partial, perspective view of an expansion filter column of the extraction apparatus of FIG. 1.

The expansion/filter column 80 may further include a molecular sieve desiccant filter (such as a 3A 89X12 desiccant) media 87 located and filling at least a portion of the inner chamber of the column 80 for insuring all water and/or condensation (and thus any potential source of oxygen) is completely removed from the solvent returning to the solvent tank 20. The desiccant filter media 87 may have a generally crystalline composition and may be particularly useful for absorbing and removing all water and condensation from the gaseous vapor solvent before it exits the expansion/filter column 80.

The expansion/filter column 80 may include a lower end cap 81 including an outlet 85 coupled to a hose 15 and the other end of the hose 15 may be coupled to the inlet of the hydrocarbon recovery pump 90. The hydrocarbon recovery pump 90 draws the gaseous solvent from the expansion/filter column 80 and returns the hydrocarbon solvent to the solvent tank 20 where the hydrocarbon solvent may re-condense under pressure and lowered temperature and the hydrocarbon solvent is again in a liquid state and the entire process may be repeated with the same material in the material column 30 or with new material. The present extraction apparatus 10 allows for the same solvent to be reused or it may be removed as a liquid and new solvent may be added.

The extraction apparatus 10 may be operated in a passive mode without the use of the hydrocarbon recovery pump 90 and by directly coupling the outlet of the expansion/filter column 80 to the inlet of the solvent tank 20. The warming effect of the recirculating heat 110 may be sufficient to vaporize the hydrocarbon solvent and return it to the solvent tank 20 but will necessarily take a far greater amount of time without the use of the hydrocarbon recovery pump 90.

Based upon limited examples, the passive mode operation will take greater than approximately 7 hours for approximately 18 pounds of liquid solvent to be vaporized and re-condensed in the solvent tank 20. Similarly, based upon limited examples, the use of the hydrocarbon recovery pump 90 reduces the recovery time to approximately 90 to 120 minutes for approximately 18 pounds of liquid solvent to be vaporized and re-condensed in the solvent tank 20. Because the desired constituents of the material may be used for human consumption, it may be desired to use a food grade hydrocarbon recovery pump 90.

Once the desired extracted components of the plant material are extracted and deposited in the collection bowl 70 with the solvent (after the unwanted lipids and other coagulated constituents are removed in the lipid filtering column 40) and after the solvent is removed/boiled off and returned to the solvent tank 20, the collection bowl 70 may either be easily removed from the collection chamber 60 and the desired extracted constituent materials and components may be stored and/or used as desired or the extracted components of the plant material may be removed from the bowl 70 using a connected outlet.

While a particular embodiment of the present invention has been shown and described, it may be to be understood that the present invention may be not limited to the embodiments described above, but encompasses any and all embodiments within the scope of the following claims.

What is claimed is:

1. A closed-loop extraction apparatus for extracting constituent components from a plant material by exposing them to a solvent, the closed-loop extractor apparatus comprising:
   a solvent tank for receiving and collecting the solvent;
   a material tank for receiving the plant material and for receiving a liquid solvent from the solvent tank and exposing the plant material to the solvent for extracting constituent components from the plant material;
   a collection tank for receiving the solvent from the material tank including the extracted constituent components; and
   a cooled, inline lipid coagulation apparatus coupled between the material tank and the collection tank.

2. The closed-loop extraction apparatus of claim 1, including a hydrocarbon recovery pump coupled to receive the heated solvent form the collection tank and pump it into the solvent tank.

3. The closed-loop extraction apparatus of claim 1, wherein the solvent tank is a jacketed solvent tank and wherein the material column is a jacketed material column and the apparatus further comprising a cryogenic chiller coupled to the jacket of the solvent tank and to the jacket of the material column and cools the solvent tank in the material column.

4. The closed-loop extraction apparatus of claim 2, wherein the solvent tank is a jacketed solvent tank and wherein the material column is a jacketed material column and the apparatus further comprising a cyrogenic chiller coupled to the jacket of the solvent tank and to the jacket of the material column and cools the solvent tank and the material column.

5. The closed-loop extraction apparatus of claim 1, wherein said solvent is a non-polar solvent.

6. The closed-loop extraction apparatus of claim 1, said closed-loop extraction apparatus further comprising a wheeled mounting rack, wherein said solvent tank, said material tank, and said collection tank are positioned on said wheeled mounting rack.

7. The closed-loop extraction apparatus of claim 1, wherein said solvent is a light hydrocarbon solvent.

8. The closed-loop extraction apparatus of claim 1, said closed-loop extraction apparatus further comprising an expansion filter tank, a recovery pump, and a recirculating heater.

9. The closed-loop extraction apparatus of claim 1, said closed loop extraction apparatus further comprising a recovery pump that provides for returning solvent to said solvent tank.

10. The closed-loop extraction apparatus of claim 1, said closed loop extraction apparatus further comprising a shutoff valve for isolating said solvent tank.

11. The closed-loop extraction apparatus of claim 1, said closed loop extraction apparatus further comprising a vacuum pump coupled to said solvent tank, wherein said vacuum pump provides for removing oxygen.

12. The closed-loop extraction apparatus of claim 1, wherein said cooled, inline lipid coagulation apparatus includes a coiled tubing within a chamber.

13. The closed-loop extraction apparatus of claim 1, wherein said cooled, inline lipid coagulation apparatus includes a chamber cooled to between −40° F. and −120° F.

14. The closed-loop extraction apparatus of claim 1, wherein the constituent components include a specific cannabinoid.

15. The closed-loop extraction apparatus of claim 1, wherein said cooled, inline lipid coagulation apparatus includes a filter stack space that holds a filter.

\* \* \* \* \*